United States Patent
Torres

(10) Patent No.: US 6,696,063 B1
(45) Date of Patent: Feb. 24, 2004

(54) TREATMENT OF HIV-ASSOCIATED DYSMORPHIA/DYSMETABOLIC SYNDROME (HADDS) WITH OR WITHOUT LIPODYSTROPHY

(75) Inventor: Ramon A. Torres, New York, NY (US)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/475,989

(22) Filed: Dec. 30, 1999

Related U.S. Application Data
(60) Provisional application No. 60/114,389, filed on Dec. 30, 1998.

(51) Int. Cl.$^7$ .......................... A61K 39/00; C07K 17/00
(52) U.S. Cl. .......................... 424/198.1; 514/2; 530/399
(58) Field of Search .......................... 424/172.1, 198.1; 435/69.4, 463; 514/2; 530/350, 399

(56) References Cited

U.S. PATENT DOCUMENTS

| | | |
|---|---|---|
| 4,588,585 A | 5/1986 | Mark et al. |
| 4,737,462 A | 4/1988 | Mark et al. |
| 4,904,584 A | 2/1990 | Shaw |
| 4,959,314 A | 9/1990 | Mark et al. |
| 4,965,195 A | 10/1990 | Namen et al. |
| 5,017,691 A | 5/1991 | Lee et al. |
| RE33,653 E | 7/1991 | Mark et al. |
| 5,116,943 A | 5/1992 | Koths et al. |
| 5,137,872 A * | 8/1992 | Seely et al. .................... 514/12 |
| 5,534,617 A | 7/1996 | Cunningham et al. |
| 5,597,709 A | 1/1997 | Rosen et al. |
| 5,597,797 A * | 1/1997 | Clark .......................... 514/12 |
| 5,612,470 A | 3/1997 | Thorner et al. |
| 5,633,352 A | 5/1997 | Dalbøge et al. |
| 5,635,604 A | 6/1997 | Dalbøge et al. |
| 5,654,010 A | 8/1997 | Johnson et al. |
| 5,688,666 A | 11/1997 | Bass et al. |
| 5,696,089 A | 12/1997 | Felix et al. |
| 5,712,380 A | 1/1998 | Kendall et al. |
| 5,721,250 A | 2/1998 | Morriello et al. |
| 5,721,251 A | 2/1998 | Chen et al. |
| 5,723,616 A | 3/1998 | Houghton et al. |
| 5,726,307 A | 3/1998 | Schoen et al. |
| 5,726,319 A | 3/1998 | Lin et al. |
| 5,731,317 A | 3/1998 | Lu et al. |
| 5,767,085 A | 6/1998 | Johansen et al. |
| 5,767,118 A | 6/1998 | Nargund et al. |
| 5,767,124 A | 6/1998 | Draper et al. |
| 5,773,441 A | 6/1998 | Hipskind et al. |
| 5,776,901 A | 7/1998 | Bowers et al. |
| 5,777,112 A | 7/1998 | Nargund et al. |
| 5,792,747 A | 8/1998 | Schally et al. |
| 5,795,957 A | 8/1998 | Deghenghi et al. |
| 5,798,337 A | 8/1998 | Somers et al. |
| 5,804,578 A | 9/1998 | Chakravarty et al. |
| 5,807,985 A | 9/1998 | Deghenghi et al. |
| 5,830,433 A | 11/1998 | Dean et al. |
| 5,834,598 A | 11/1998 | Lowman et al. |
| 5,843,453 A | 12/1998 | Holder et al. |
| 5,846,936 A | 12/1998 | Felix et al. |
| 5,847,066 A | 12/1998 | Coy et al. |
| 5,849,535 A | 12/1998 | Cunningham et al. |
| 5,849,700 A | 12/1998 | Sørensen et al. |
| 5,849,704 A | 12/1998 | Sørensen et al. |
| 5,851,992 A | 12/1998 | Sørensen |

FOREIGN PATENT DOCUMENTS

EP 0075444 B1 3/1983

OTHER PUBLICATIONS

Krentz et al. 1993. Anthropometric, metabolic and immunological effects of recombinant growth hormone in AIDS and AIDS–related complex. J Acquire Immune Defic Syndr. vol. 6. No. 3, pp. 245–251.*

Windisch et al. 1998. Recombinant human growth hormone for AIDS–associated wasting. Ann Pharmacother. vol. 1 32. No. 4, pp. 437–445.*

James et al. 1998. Successful treatment of "buffalo hump" with growth hormone AIDS treatment news. No. 298, pp. 5–6.*

Maus et al. 1998. Successful treatment of PI–induced visceral abdominal fat accumulation with R–human growth hormone. AIDS. vol. 12. Sup 4. P145.*

Mayo. 1992. Mol. Endocrinology., 6, 1734–1744.*

DeNoto et al. 1991. Nucleic Acids Research., 9(15), 3719–3730.*

Jones et al., "Crystallization of authentic recombinant human growth hormone", *Biotechnology*, 5:499–500 (1987).

Martial et al., "Human growth hormone: complementary DNA cloning and expression in bacteria", *Science*, 602–607 (1979).

Bewley et al., "Sequence comparison of human pituitary growth hormone, human chorionic somatomammotropin, and ovine pituitary growth and lactogenic hormones", *Int. J. Peptide Protein Res.*, 4:281–287 (1972).

(List continued on next page.)

*Primary Examiner*—James Housel
*Assistant Examiner*—Shanon Foley
(74) *Attorney, Agent, or Firm*—Browdy and Neimark

(57) ABSTRACT

Pathological regional adipose tissue accumulation associated with HIV-associated dysmorphic/dysmetabolic syndrome (HADDS) which may occur with or without subcutaneous adipose tissue lipodystrophy (and which is also described as HIV-associated adipose redistribution syndrome or HARS and other specific medical terms), is treated by administering an effective amount of human growth hormone or other substance which binds to and initiates signalling of the hGH receptor. Alternatively, a substance which stimulates production of endogenous hGH, such as human growth hormone releasing hormone, may be administered. HADDS and related syndromes include abnormal adipose tissue accumulation in the visceral, submandibular, supraclavicular, pectoral, mammary and/or dorsocervical (buffalo hump) area, and/or with subcutaneous lipomas, with or without associated metabolic or other physiologic abnormalities.

27 Claims, No Drawings

OTHER PUBLICATIONS

Abstract 010—Cheng, " Lipodystrophy in HIV; a community perspective" (1999).

Cunningham et al., "Dimerization of human growth hormone by Zinc", *Science*, 253:544–548 (1991).

Abstract 006—Engelson et al., "Effect of recombinant human growth hormone in the treatment of visceral fat accumulation in HIV infection: interim analysis" (1999).

Abstract 336*/32173—Kotler et al., "Alterations in body fat distribution in HIV–infected men and women" *12 World AIDS Conference Geneva* (Jun. 28–Jul. 3, 1998).

Abstract 002—Muurahainen et al., "The SALSA (self–ascertained lipodystrophy syndrome assessment) cohort: abnormalities in cases compared to controls" (1999).

Abstract 063—Muurahainen et al., "Abnormalities in HIV–associated lipodystrophy syndrome that vary by weight status" (1999).

Abstract 177*/12373—Dong et al., "Changes in body habitus in HIV(+) women after initiation of protease inhibitor therapy" (1998).

Carr et al., $5^{th}$ Conference on Retroviruses and Opportunistic Infections "A syndrome of peripheral lipodystrophy (LD), hyperlipidemia and Insulin resistance due to HIV protease inhibitors (PI's)", Chicago, IL, p. 410 (Feb. 1–6, 1998).

Mulligan et al., $5^{th}$ Conference on Retroviruses and Opportunistic Infections "Evidence of unique metabolic effects of protease inhibitors", Chicago, IL, p. 414 (Feb. 1–5, 1998).

Keruly et al., $5^{th}$ Conference on Retroviruses and Opportunistic Infections "Diabetes and hyperglycemia in patients receiving protease inhibitors", Chicago, IL, p. 415 (Feb. 1–5, 1998).

Dong et al., $5^{th}$ Conference on Retroviruses and Opportunistic Infections "Diabetes and use of protease inhibitors", Chicago, IL, p. 416 (Feb. 1–5, 1998).

Lo et al., "Buffalo hump" In men with HIV–1 infection, *The Lancet*, 351:867–870 (Mar. 21, 1998).

Miller et al., "Visceral abdominal–fat accumulation associated with use of indinavir", *The Lancet*, 351:871–875 (Mar. 21, 1998).

Viraben et al., "Indinavir–associated lipodystrophy", *AIDS*, 12:F37–F39 (1998).

Adelman et al., "In vitro deletional mutagenesis for bacterial production of the 20,000–Dalton form of human pituitary growth hormone", *DNA*, 2:183–193 (1983).

Albertsson–Wikland et al., "Daily subcutaneous administration of human growth hormone in growth hormone deficient children", *Acta Poediatr Scand*, 75:89–97 (1986).

Becker et al., "Chemical physical, and biological characterization of a dimeric form of biosynthetic human growth hormone", *Biotechnology and Applied Biochemistry*, 9:478–487 (1987).

Bewley et al., "The chemistry of human pituitary growth hormone", *Adv. Emzymol, Related Areas*, 42:73–166 (1975).

Denoto et al., "Human growth hormone DNA sequence and mRNA structure: possible alternative splicing", *Nucleic Acids Research*, 9:3718–3731 (1981).

Hendricks et al., "Plasma clearance of intravenously administered pituitary human growth hormone: gel filtration studies of heterogeneous components", *Journal of Clinical endocrinology and Metabolism*, 60:864–867 (1985).

Jørgensen et al., "Serum profiles and short–term metabolic effect of pituitary and authentic biosynthetic human growth hormone in man a double–blind cross–over study", *Acta Endocrinologica (Copenh)*, 116:381–386 (1987).

Jørgensen et al., "Pharmacokinetics of biosynthetic and pituitary human growth hormones in rats", *Pharmacology & Toxicology*, 63:129–134 (1988).

Lewis et al., "An interchain disulfide dimmer of human growth hormone*", *The Journal of Biological Chemistry*, 252:3697–3702 (1977).

Lewis et al., "Enhancement of the hyperglycemic activity of human growth hormone by enzymic modification", *Endo.* 101:1587–1603 (1977).

Lewis et al., "Human Growth hormone; additional members of the complex*", *Endo*, 104:1256–1265 (1979).

Lewis et al., "Altered proteolytic cleavage of human growth hormone as a result of deamidation", *The Journal Of Biological Chemistry*, 256:11645–11650 (1981).

Ho et al., "Indinavir–associated facial lipodystrophy in HIV–infected patients", *AIDS Patient Care and STDs*, 13:11–16 (1999).

Kosmiski et al., "An increase in abdominal girth on protease inhibitor therapy is associated with visceral obesity and metabolic disturbances that closely resemble syndrome", $1^{st}$ *International Workshop on Adverse Drug Reactions and Lipodystrophy in HIV*, 49–55 (1999).

Henry et al., "Atorvastatin and gemfibrozil for protease–inhibitor–related lipid abnormalities", *The Lancet*, 352:1031–1035 (1998).

Engelson et al., "Altered body fat distribution in HIV infection:regional body composition measurements by whole body MRI and DXA scans", $12^{th}$ World AIDS Conference Geneva, 471–471 (Jun. 28–Jul. 3, 1998).

Henry et al., "Severe premature coronary artery disease with protease inhibitors", *The Lancet*, 351:1328 (1998).

Carr et al., "Pathogenesis of HIV–1–proteases inhibitor–associated peripheral lipodystrophy, hyperlipidaemia, and insulin resistance", *The Lancet*, 351:1881–1883 (1998).

Carr et al., "A syndrome of peripheral lipodystrophy, hyperlipidaemia and insulin resistance in patients receiving HIV protease inhibitors", *AIDS*, F51–F58 (1998).

Brinkman et al., "The first international workshop on adverse drug reactions and lipodystrophy in HIV session 4: related syndromes mitochondrial toxicity of nucleosides" *The Body: An AIDS and HIV Information Resource*, Abstract No. 9 (1999).

Abstract—Torres et al., "The effect of recombinat human growth hormone on protease–inhibitor–associated fat maldistribution syndrome", 675.

Abstract—Viard et al., "Lipodystrophic syndromes in a cohort of HIV–1–infected patients receiving HAART with a protease inhibitor", Abstract No. 026.

Wanke et al., "Recombinant human growth hormone improves the fat redistribution syndrome (lipodystrophy) in patients with HIV", *AIDS*, 2099–2103 (1999).

Abstract 031—Ruiz et al., "A multicentre, randomized, open–label, comparative trial of the clinical, immunological and virological benefit of switching thePl by nevirapine in HAART–experienced patients suffering lipodystrophy", 35.

Abstract 068—Rozenbaum et al., "Prospective follow–up of a Pl substitution for efavirenz in patients with HIV–related lipodystrophy syndrome".

Abstract 054—Molyle et al., "Changes in visceral adipose tissue and blood lipids in persons reporting fat redistribution syndrome switched from Pl therapy to efavirenz".

Miller et al., "Visceral abdominal–fat accumulation associated with use of indinavir", *The Lancet*, 351:871–875 (1998).

Abstract 042—Milano et al., "Two case reports of unusual lipomatous growths associated with combination antiretroviral therpay".

Abstract 038—Maggi et al., "Precvocious lesions of the carotid vessels in HIV–1–infected patients treated with proteast inhibitors".

Abstract 018—Mercie et al, "Case report of lipidystrophy observations in patients naive of protease inhibitor treatment, anquitaine cohort".

Krentz et al., "Anthropometric, metabolic, and immunological effects of recombinant human growth hormone in AIDS and AIDS–related complex", *Journal of Acquired Immune Deficiency Syndromes*, 6(3)245–251 (1993).

Engelson et al., Fat distribution in HIV–infected patients reporting truncal enlargement quantified by whole–body magnetic resonance imagining[1-3], *Am J Clin Nutr*, 69:1162–1169 (1999).

Becker et al., "A nondiabetogenic derivative of human growth hormone", 342:108.

Bjorntorp et al., "Review the regulation of adipose tissue distribution in humans", *International Journal of Obesity*, 20:291–302 (1996).

Carr et al., "Diagnosis, prediction, and natural course of HIV–1 protease–inhibitor–associated lipodystrophy, hyperlipidaemia, and diabetes mellitus: a cohort study", *The Lancet*, 353:2093–2099 (1999).

Chen et al., "The human growth hormone locus: nucleotide sequence, biology, and evolution", *Genomics*, 4:479–497 (1989).

Abstract 006—Engelson et al., "Effect of recombinant human growth hormone in the treatment of visceral fat accumulation in HIV infection: interim analysis", *Antiviral Therapy*, 4(Supplement 2):19 (1999).

Hsiung et al., "Use of bacterioncin release protein in *E. Coli* for excretion of human growth hormone into the culture medium", *Bio/technology* 7:267–271 (1989).

Jones et al., "Crystallization of authentic recombinant human growth hormone", *Bio/technology*, 5:499–500 (1987).

Lewis et al., "A naturally occurring structural variant of human growth hormone", *The Journal of Biological Chemistry*, 253:2679–2687 (1978).

Lewis et al., "Altered proteolytic cleavage of human growth hormone as a result of deamidation", *The Journal of Biological Chemistry*, 11645–11650 (1981).

Zurek et al., "Human growth hormone: complementary DNA cloning and expression in bacteria", *Science* 205:602–607 (1979).

Abstract P145—Mauss et al., "Successful treatment of Pl–induced visceral abdominal–fat accumulation with R–human growth hormon".

Mocroft et al., "Changes in AIDS–defining illnesses in a London clinic, 1987–1998", *Journal of Acquired Immune Deficiency Syndromes and Human Retrovirology*, 21:401412 (1999).

Moore et al., "Equivalent potency and pharmacokinetics of recombinant human growth hormones with or without an N–terminal methionine", *Endocrinology*, 122:2920–2926 (1988).

Windisch et al., "Recombinant human growth hormone for AIDS–associated wasting", *The Annals of Pharmacotherapy*, 32:437–445 (1998).

Kotler et al., "Studies of body composition and fat distribution in HIV–infected and control subjects", *Journal of Acquired Immune Deficiency Syndromes and Human Retrovirology*, 20:228–237 (1999).

Pineda, "Predictable upwelling and the shoreward transport of planktonic larvae by internal Tidal Bores", *Science*, 548.

Carr et al., "Pathogenesis of HIV–1–protease inhibitor–associated peripheral lipodystrophy, hyperlipidaemia, and insulin resistance" *The Lancet*, 351:1881–1883 (1998).

Carr et al., "Fast track a syndrome of peripheral lipodystrophy, hyperlipidaemia and insulin resistance in patients receiving HIV protease inhibitors", *AIDS*, 12:F51–F58 (1998).

Michaels et al., "Differences in the Incidence rates of opportunistic processes before and after the availability of protease inhibitors", *5th Conference on Retroviruses and Opportunistic Infections*, (Feb. 1–5, 1998).

Dong et al., "Diabetes and use of protease inhibitors", *12th World Aids Conference Geneva*, (Jun. 28–Jul. 3, 1998).

Abstract No. PB0895—Muurahainen et al., Detection of occult wasting by BIA technology, *International Conference AIDS*, 10(2)220 (Aug. 7–12, 1994).

Viraben et al., "Fast Track indinavir–associated lipodystrophy", *AIDS*, 12::F37–F39 (1998).

Lewis et al., "The 20,000–Dalton variant of human growth hormone' location of the amino acid deletions", *Biochemical and Biophyscial Research Communications*, 92:511–516 (1980).

Bjorntorp et al., "Abdominal obesity and the development of noninsulin–dependent diabetes mellitus", *Diabetes/Metabolism Reviews*, 4:615–622 (1998).

\* cited by examiner

TREATMENT OF HIV-ASSOCIATED DYSMORPHIA/DYSMETABOLIC SYNDROME (HADDS) WITH OR WITHOUT LIPODYSTROPHY

CROSS-REFERENCE TO RELATED APPLICATION

The present application claims the benefit of provisional application No. 60/114,389, filed Dec. 30, 1998, the entire contents of which being hereby incorporated herein by reference.

FIELD OF THE INVENTION

The present invention is directed to a method for treating HIV-associated dysmorphia/dysmetabolic syndrome or HIV-associated adipose redistribution syndrome, and related syndromes.

BACKGROUND OF THE INVENTION

Advances in antiviral treatment of HIV infection, along with developments in the prophylaxis and therapy of opportunistic infections, have greatly improved the long-term health of HIV-infected individuals. However, along with improved antiretroviral therapy a new syndrome has developed, which is identified herein as HIV-associated dysmorphia/dysmetabolic syndrome, or HIV-associated adipose redistribution syndrome (HARS), or hereafter abbreviated HADDS.

HADDS involves pathological accumulation of adipose tissue in specific regional depots. The pathologic adipose tissue accumulation of HADDS may also be associated with abnormal adipose tissue depletion elsewhere (lipodystrophy or lipoatrophy), with or without associated metabolic abnormalities, premature atherosclerotic lesions, depletion of lean body mass, and/or other abnormal physiology.

This recently discovered clinical disorder, which has been referred to by a number of terms, including HIV lipodystrophy syndrome and other terminology, has important public health consequences, as described further below.

HADDS patients typically present with abnormal accumulation of adipose tissue in the abdomen, specifically in the visceral adipose tissue compartment (Miller et al, 1998, Kotler et al, 1999; Engelson et al, 1999). HADDS patients may also present with abnormal adipose tissue accumulation in the dorsocervical area ("buffalo hump"), the submandibular area ("horse collar"), the pectoral, mammary, and/or supraclavicular areas, and/or with subcutaneous lipomas (encapsulated benign fatty tumors, single or multiple).

Abnormal, involuntary, pathological, and often dysmorphic accumulation of adipose tissue is sufficient to diagnose a HIV-infected patient with HADDS. However, in addition to developing abnormal adipose accumulation, some HADDS patients develop abnormally depleted subcutaneous adipose tissue, termed "peripheral lipodystrophy" (or lipoatrophy) at other specific sites. This adipose depletion is typically observed in the face (buccal, parotid, and periauricular fat pads), and in the subcutaneous adipose tissue surrounding the limbs, trunk, and/or gluteal regions. Also, some HADDS patients may present with metabolic abnormalities (Carr et al, 1998a, 1998b, 1999a, 1999b; Lipodystrophy Rapid Report, 1999).

The metabolic abnormalities associated with HADDS and lipodystrophy syndrome typically involve disordered lipid and glucose metabolism. Clinical manifestations may include fasting hypertriglyceridemia, hyperlipidemia, and abnormalities of the insulin/glucose axis (elevated fasting insulin, elevated C-peptide, insulin resistance or reduced insulin sensitivity), with or without overt diabetes (Carr et al, 1998a, 1998b, 1999a, 1999b; Henry et al, 1998; Grunfeld, 1999).

Abnormal adipose tissue accumulation abnormalities occur more frequently in female than male cases diagnosed with HADDS, while fat depletion, hyperglycemia, and hyperlipidemia are more commonly observed in male cases (Muurahainen, 1999). Hence the presentation of HADDS appears to vary by gender.

There are preliminary reports suggesting that patients with HADDS exhibit preclinical evidence of increased risk for coronary heart disease (CHD). Preclinical indicators of CHD include increased coronary artery calcification (CAC) as quantified by electron beam computed tomography (EBCT), and extracoronary indicators such as increased intima media thickening (IMT) in the carotid artery and impaired blood flow-mediated dilation in the brachial artery, as quantified by ultrasonography, which signify endothelial dysfunction that may lead to atherosclerosis and CHD. In eight patients with HADDS who developed increased abnormal girth with abnormally accumulated visceral adipose tissue after initiation of HIV rotease inhibitor (PI) therapy who underwent EBCT, Kosmiski et al (1999) reported a mean CAC score consistent with minimal identifiable plaque burden. There are also preliminary reports indicating that HIV patients receiving PIs display abnormal carotid IMT (Maggi et al, 1999) and impaired brachial flow-mediated dilation (Stein, 1999), signifying endothelial dysfunction. However, it is unclear which, if any, of the patients in the two aforementioned preliminary reports were HADDS patients, and what percentage of HADDS patients have preclinical indicators of abnormal endothelial function.

There have also been case reports of premature coronary artery disease in HIV patients under age forty who have been receiving combination antiretroviral therapy that include a protease inhibitor (Henry et al, 1998). However, it may take years before well-designed, prospective, observational cohort studies precisely quantify the risk of premature coronary artery disease in patients with HADDS.

Some patients with HADDS also exhibit involuntary weight loss with depletion of lean body mass (AIDS wasting or cachexia), and possibly depletion of lean body mass without overt weight loss (occult wasting) (Muurahainen, unpublished observations, data on file, Serono Laboratories, Norwell, Mass.).

Other abnormal physiology that may be observed in patients with HADDS or lipodystrophy syndrome include gout and pancreatitis (presumably resulting from severe hypertriglyceridemia), hepatic steatosis (possibly reflecting chronic lactic acidosis), hypogonadism, and possibly other hormonal abnormalities (Henry et al, 1998; Brinkman, 1999; Lipodystrophy Rapid Report, 1999).

HADDS and lipodystrophy syndrome may or may not be associated with other abnormalities, such as cutaneous abnormalities (such as thinning hair, hair loss, hair brittleness, dry skin, abnormal nails, ingrown toenails), disorders of the coagulation syndrome that result in increased bleeding in hemophiliacs, osteoporosis or avascular necrosis of the hips, peripheral neuropathy, nausea, fatigue, weight loss, chronic diarrhea, fever, mennorhagia and menstrual abnormalities, impaired sexual dysfunction (decreased libido, erectile dysfunction), and abnormalities of the genitalia resembling Peyronie's Disease (Carr et al, 1998a, 1998b, 1999a, 1999b; Lipodystrophy Rapid Report, 1999).

In sum, HADDS is a recently discovered multisystemic, gender dimorphic disorder associated with HIV infection that includes (1) regional changes in adipose distribution, frequently dysmorphic, that result from abnormal regional accumulation of adipose tissue, with or without lipodystrophy, (2) occasionally observed in conjunction with abnormalities of lipid and glucose metabolism, and (3) possibly associated with other physiologic abnormalities, including premature atherosclerotic lesions, depletion of lean body mass, and other abnormalities.

Since HADDS and HIV-associated lipodystrophy syndrome have only recently been described, standardized nomenclature or consensus definition(s) for these syndromes are lacking. Kotler and Schambelan (1999) predict that we may eventually see an official case definition that has major and minor criteria, similar to what is already in place for rheumatic disorders such as systemic lupus erythematosis (Kotler and Schambelan, 1999).

In recent years, a plethora of terms and nomenclature have been used by scientists, clinicians, and patient advocates to describe the syndrome and its manifestations. Any of the manifestations may be observed in men, women, and children with HIV infection who develop the syndrome. The terms describing it may be found in the peer-reviewed scientific literature, posted in discussions and reviews on the internet. The terms provided below are non-inclusive. New terms are continually added.

Terms that have been used to describe the syndrome or subsets of it include: HIV-associated dysmorphia/dysmetabolic syndrome (HADDS); HIV-associated adipose redistribution syndrome (HARS); lipodystrophy syndrome and HIV-associated lipodystrophy syndrome (HALS); HIV-related peripheral lipodystrophy (HIPL); HIV-associated fat redistribution syndrome (HIVFRES) or fat redistribution syndrome (FRS); fat maldistribution syndrome (FMS), HIV-associated dysmorphia/metabolic Syndrome (HADMS), abnormal body fat (ABF) accumulation, and protease inhibitor-associated lipodystrophy (PI-AL).

Terms used to describe abnormal accumulation of abdominal adipose tissue in patients with the syndrome include: HIV-associated "Crix belly" and "protease paunch" (although the truncal adiposity may not be directly related to Crixivan or other protease inhibitors); "pouch belly"; truncal adiposity, truncal obesity, central obesity, abdominal adiposity, increased waist to hip ratio (WHR), increased waist-to-thigh circumference ratio (by anthropometry), increased truncal to limb fat ratio (by DXA scan), increased abdominal visceral adipose tissue (VAT) with decreased subcutaneous adipose tissue (SAT) and increased VAT/SAT ratio by CT or MRI scan, and "Pseudo-Cushing's syndrome".

Terms used to describe other types of fat accumulation in patients with HADDS include HIV-related buffalo hump, abnormal accumulation of dorsocervical fat, "dorsocervical lipodystrophy" (a misnomer because it implies depletion of the dorsocervical fat pad), increased neck fat, facial fat accumulation, double chin, moon face, submandibular fat accumulation ("horse collar"), supraclavicular fat pad accumulation, multiple symmetric lipomatosis, "lumps and bumps", Madelung's syndrome, HIV-related breast enlargement, mammary fat hyperplasia and gynecomastia. (Note that it is unclear if there is true gynecomastia, or whether there is hypertrophy of subcutaneous chest fat other than mammary tissue), "chest fat accumulation", and peripheral adiposity.

Terms used to describe abnormal depletion of adipose tissue found in some patients with HADDS and lipodystrophy syndrome include: pseudocachexia, peripheral lipodystrophy, pure lipoatrophy, "Lipo", facial wasting, facial wrinkling, sunken cheeks, sunken eyes, temple hollowness, prominent zygomatic arch, "cadaveric facies", buccal, parotid, and periauricular fat pad wasting, limb wasting, skinny, stick arms and stick legs with symmetrical, prominent non-varicose veins, muscularity and bones, butt wasting, saggy buttocks with loose skin folds, loss of buttock fat contour, and hollowing of the buttocks.

For the purpose of the invention described herein, a distinction is made between HADDS and HIV lipodystrophy syndrome. Several types of HIV-related lipodystrophy syndrome(s) have been described: patients presenting only with adipose tissue accumulation, those presenting adipose accumulation and depletion ("mixed syndrome"), and those presenting only with adipose tissue depletion ("pure lipoatrophy") (Rosenbaum, 1999; Saint-Marc, 1999; Thiebaut et al, 1999; Viard, 1999).

For the purpose of the invention described herein, HADDS patients are considered to be a subset of patients with HIV-related lipodystrophy syndrome who exhibit abnormal adipose tissue accumulation. HADDS patients are lipodystrophy patients who exhibit either adipose accumulation alone or adipose accumulation associated with adipose depletion elsewhere ("mixed syndrome"). The rationale for focusing on HADDS patients as a clinically important subset of patients with lipodystrophy syndrome, is that patients with abnormally accumulated adipose tissue are the ones for whom the invention, a lipolytic (adipose-depleting) agent, will be recommended as a treatment, in contrast to patients with lipodystrophy syndrome who exhibit only adipose tissue depletion, or pure lipoatrophy.

For purposes of the invention described herein, it makes sense from a scientific perspective to focus on the treatment of pathologically accumulated adipose tissue with associated metabolic and physiologic abnormalities, rather than to focus on treatments for depleted adipose tissue. As discussed further below, excess accumulation of visceral adipose tissue has been associated with adverse clinical outcomes. The long term clinical consequences of adipose tissue depletion alone (pure lipoatrophy per se), if any, are presently unknown.

Since 1997, the unusual and unexpected morphologic features that comprise HADDS and HIV-related lipodystrophy syndrome have been increasingly observed and reported. Manifestations of the syndrome were first observed in conjunction with use of highly active combination antiretroviral therapies that included an HIV protease-inhibiting agent (Carr et al, 1998a, 1998b, 1999a, 1999b; Lo et al, 1998), but the manifestations have also been observed in HIV patients who have never received protease inhibitors (Lo et al, 1998; Kotler, 1998; Carr et al, 1999a, 1999b; Mercie et al, 1999; Gervasconi, 1999; Hadigan et al, 1999; Brinkman, 1999).

Abnormal adipose tissue accumulation, the primary pathologic lesion of HADDS may develop rapidly (within weeks to months after initiating a new antiretroviral regimen) or may develop gradually over periods of one to several years. The etiology of the syndrome is unknown. It is unclear whether the HADDS and lipodystrophy syndromes are drug-related, related, and if they are drug-related, what antiretroviral agents or classes of agents are causal. Both HIV-1 protease inhibitors and HIV-1 reverse transcriptase inhibitors have been proposed as etiologic agents (Carr et al, 1998a, 1998b, 1999a, 1999b; Saint-Marc, 1999; Brinkman, 1999).

Although manifestations of HADDS and lipodystrophy syndrome are more prevalent in HIV/AIDS patients who have received combination antiretroviral therapies (especially highly active antiretroviral therapy with protease inhibitors), in some cases the syndrome or some of its manifestations have been observed in patients who have never received antiretrovirals (Lo et al, 1998; Carr et al, 1998a, 1998b, 1999a, 1999b; Mercie et al, 1999).

Manifestations of the syndrome sometimes partially abate when antiretroviral medications are discontinued or changed, but the manifestations often do not abate completely or resolve relatively for many months or up until a year after the switch in therapy (Saint-Marc, 1999; Rosenbaum, 1999; Ruiz, 1999; Moyle; 1999, Gatell; 1999). This raises a concern that the syndrome might occur in conjunction with immune reconstitution or autoimmune phenomena associated with chronic suppression of HIV-1 (Kotler, 1998).

As mentioned previously, for a number of reasons the dysmorphic bodily changes and metabolic manifestations of HADDS are of important public health significance. Abnormal adipose accumulation becomes clinically significant when it results in physical discomfort or disability due to a variety of symptoms, including the following types of symptoms: headaches and inability to fully extend the neck due to buffalo hump; abdominal cramping, indigestion, constipation, shortness of breath and respiratory insufficiency, or ventral hernias due to rapid accumulation of excess visceral adipose tissue. Abnormal accumulation of visceral adipose tissue is also a significant independent risk factor for cardiovascular disease.

The physical manifestations of HADDS are also of public health significance because these manifestations are perceived by many patients to be disturbing, disfiguring, appalling, stigmatizing, and/or threatening loss of privacy. Some patients with the syndrome develop body image disturbance, depression, and agoraphobia (Cheng, 1999; Forum for HIV Collaborative Research, 1999). The unusual and increasingly well-recognized physical characteristics of HADDS such as buffalo hump, truncal obesity, breast enlargement, horse collar, supraclavicular fat pads, facial and limb wasting, and lipomas have the potential to become socially stigmatizing because these recognizable features instantly reveal that a patient probably has HIV/AIDS ("a forced form of HIV identification", according to Cheng (1999), as cited in Lipodystrophy Rapid Report (1999)).

Concerns about health, appearance, potential stigmatization and loss of privacy in the workplace and elsewhere, may lead some patients with HADDS to discontinue otherwise effective antiretroviral therapy (Struble and Piscitelli, 1999). These concerns may also lead other HIV patients to refuse to initiate medically necessary antiretroviral therapies for fear of developing the syndrome and the increased medical risks associated with it (Cheng, 1999). This could eventually lead to increased HIV infectivity, more opportunistic complications, and increased medical costs.

The increased cardiovascular risk factors associated with HADDS are also of important public health significance. These risk factors include abnormally accumulation of visceral adipose tissue, hyperlipidemia, hyperinsulinemia, and premature atherosclerotic changes associated in HADDS, may result in increased risk for cardiovascular disease and stroke (Henry et al, 1998).

Other metabolic manifestations associated with HADDS syndrome also have the potential to become medically significant problems warranting therapeutic intervention. These metabolic manifestations include sudden, severe hyperglycemia, new-onset diabetes mellitus, pancreatitis and gout due to pronounced hypertriglyceridemia, and difficult-to-manage hyperlipidemia that may include elevated total cholesterol, elevated low density lipoprotein (LDL) cholesterol, and decreased high density lipoprotein (HDL) cholesterol, and other lipoprotein abnormalities associated with increased cardiovascular risk (Henry et al, 1998).

With respect the invention described herein, it is worth noting that antiretroviral agents (especially HIV protease inhibitors) undergo substantial hepatic metabolism. It is difficult to pharmacologically manage hyperlipidemia and hyperinsulinemia in HIV patients receiving combination antiretroviral therapy because the antiretroviral agents typically interact with anti-hyperlipidemics (statins, fibrates) and anti-hyperglycemic agents (thiazides and glitazones), which also undergo significant hepatic metabolism (Henry et al, 1998). A therapy such as the invention described herein, using an agent which is not primarily metabolized by the liver, and which has the potential to reduce hyperlipidemia and improves insulin sensitivity while depleting abnormally accumulated visceral adipose tissue, may be of special value in the treatment of HADDS.

Moreover, other physiologic abnormalities that have been suggested to be evaluated as part of research to develop a case definition of lipodystrophy syndrome, which may ultimately be associated with HADDS, may warrant therapeutic intervention (Lipodystrophy Rapid Report, 1999). These abnormalities include hypertension, hypogonadism, impaired sexual function (decreased, erectile dysfunction), menstrual irregularities, hair loss, dry skin, and ingrown toenails that can become infected, peripheral neuropathy, liver steatosis, osteoporosis with bone fractures and avascular necrosis of the hips, and derangement of the complement system with coagulation disorders, leading to increased bleeding in hemophiliacs.

Regarding excess adipose tissue accumulation in HADDS, the key pathological abnormality associated with this syndrome, it is worth noting that abnormal adipose accumulation is typically more pronounced regionally than in the body as a whole (Carr et al, 1998a, 1998b; Engelson et al, 1999; Kotler et al, 1999). Since regional adipose deposition in patients with HADDS may occur in conjunction with depletion of subcutaneous adipose tissue elsewhere, and/or depletion lean body mass, whole body fat accumulation and weight may not change significantly as a patient develops HADDS. It should also be noted that in order to diagnose HADDS, techniques that enable one to assess regional accumulation of adipose tissue are needed. Clinical assessment may include patient and provider history of changes in body habitus, anthropometry, serial photography, DXA, CT, and/or MRI scanning).

The most common presentation of regional fat accumulation in patients with HADDS is truncal obesity or visceral adiposity. Carr et al (1998) documented increased truncal fat in a majority (64%) of their protease inhibitor-treated subjects using the technique of dual-energy X-ray absorptiometry (DXA). Muurahainen at al (1999) found that 70 to 90% their cases reported increased abdominal girth as documented by patient self assessment questionnaire that was corroborated by physician report.

It has been demonstrated in that the truncal adipose tissue observed by DXA and increased abdominal girth reported by patients with HADDS primarily reflects abnormal accumulation of visceral adipose tissue (Miller et al, 1998; Kotler et al, 1999; Engelson et al, 1999). Miller et al (1998) reported that some patients experienced an increase in abdominal girth with symptoms of abdominal fullness, distension, or bloating after adding indinavir, a protease inhibitor, to combination drug regimens for HIV-1 infection. In several patients with these symptoms, abdominal computed-tomography (CT) scans revealed an excess amount of intra-abdominal fat and a relative paucity of subcutaneous fat.

Using whole body magnetic imaging resonance (MRI) technology to quantify abdominal fat, Kotler and colleagues reported that the increased girth in HIV patients with truncal obesity represented pathological accumulation of visceral adipose tissue in conjunction with depletion of subcutaneous adipose tissue (Kotler et al, 1998; Engelson et al, 1999). Not all of these patient received HIV protease inhibitors. The visceral adipose tissue depot included omental adipose tissue surrounding the intestines along with pelvic and perinephric adipose tissue (Engelson et al, 1999). The visceral adipose tissue (VAT) accumulation observed in patients with HADDS is typically two to seven times standard deviations above the mean for VAT in gender and age-matched healthy controls (Kotler, personal communication, 1999, manuscript in preparation).

Other types of abnormal adipose tissue accumulation in patients with HADDS include buffalo hump (dorsocervical fat pad), enlargement of the submandibular or supraclavicular fat pads with apparent bulging, lipomas (single or multiple) and increased accumulation of adipose tissue in the chest or breast area, observed more frequently in women more than in men (Dong K et al, 1998; Falutz, 1999; Gervasconi et al, 1999; Muurahainen, 1999).

Regarding buffalo hump, Lo et al (1998) reported the results of studies done in eight HIV-1-positive patients referred for investigation abnormal accumulation of adipose tissue in the dorsocervical area. Only 50% of these patients were receiving triple antiretroviral regimens that included a protease inhibitor. No other signs of Cushing's Syndrome were present in the patients. The fact that 50% of the patients with buffalo hump had no history of protease-inhibitor use indicates that development of non-Cushingoid buffalo hump is not unique to patients receiving protease-inhibitor therapy. The mechanism of further increase in triglyceride values in patients with buffalo hump is not certain, although a possible relation between increased triglyceride concentration and atypical body-fat distribution should be considered. For example, central fat accumulation may lead to the metabolic syndrome of insulin resistance, hypertriglyceridemia and hypertension if the major component gained is visceral fat.

The subcutaneous adipose tissue depletion (lipodystrophy, or lipoatrophy) that is often observed HADDS patients includes thinning of the skin on the arms and legs, with venous prominence. There is also thinning of facial fat with increased wrinkling of the face, especially in the nasolabial folds. Sometimes hollow sunken cheeks are observed. Viraben et al (1998) reported a case series involving eight patients who developed either partial or generalized lipodystrophy after protease inhibitor therapy. While two patients developed progressive loss of subcutaneous fat from both legs, excess fat deposition in the unaffected buttocks and abdomen gave an impression of obesity. In six cases, a cachetic appearance was observed resulting from the loss of buccal, parotid and preauricular fat pads. Two patients exhibited a generalized loss of fatty tissue from the face. In 50% (four) of the patients in this case series, either diabetes or insulin resistance was also discovered.

Metabolic abnormalities do not occur in every patient with HADDS, and not every HIV patient who develops metabolic abnormalities (while receiving protease inhibitors, other antiretroviral agents, or receiving no agents at all) concurrently develops abnormal fat accumulation. Mulligan et al (1998) compared results obtained in patients before and after beginning an antiretroviral regimen that included a protease inhibitor or lamivudine. No significant changes in total or regional fat or lean body mass were found by dual-energy X-ray absorptiometry in any group over the short time period of about four months. Miller et al (1998) found no relationships among CT-diagnosed visceral fat accumulation, hypertriglyceridemia, and hypercholesterolemia. Other investigators have also reported that abnormal adipose tissue accumulation in HIV patients is not always associated with hyperlipidemia or abnormal insulin/glucose metabolism (Lo et al, 1998; Muurahainen, 1999; Kotler and Schambelan; 1999).

Regarding disturbances of glucose and insulin metabolism, the FDA reported that there were reports of insulin resistance in patients receiving protease inhibitors for treatment HIV infection, and some of these diabetic patients were found to have truncal obesity (FDA, 1997). However, those who have since reviewed diabetes associated with the use of protease inhibitors have concluded that protease inhibitor-induced hyperglycemia appears to be a rare occurrence (Dong B J et al, 1998; Keruly, 1998).

With respect to fasting hypertriglyceridemia, this abnormality was first reported and associated with HIV infection, in the absence of antiretroviral therapies and abnormal adipose tissue accumulation (Grunfeld, 1992). Patients with hypertriglyceridemia prior to starting combination antiretroviral therapy appear to have an exacerbation of the condition while on combination therapy and do not return to their previous state.

With respect to hypercholesterolemia and other metabolic abnormalities in HIV patients on combination antiretroviral therapy, serum cholesterol concentrations rise, though rarely to dangerously high levels (Carr et al, 1998a, 1998b, 1999a, 1999b; Henry et al, 1998). Some patients developed hypertension and, in others, low serum testosterone concentrations developed or pre-existing hypogonadism persisted.

From the lack of tight associations described above, it is unclear if administration of protease inhibitors produces lipodystrophy syndrome or HADDS. Carr et al (1998), who described peripheral lipodystrophy and unusual fat accumulation in HIV-infected patients receiving protease inhibitors which, together with the known side effects of protease inhibitors of hyperlipidemia and diabetes mellitus, have suggested that protease inhibitors cause metabolic perturbations leading to insulin resistance. Carr also found evidence of insulin resistance in patients with lipodystrophy syndrome, although clinically apparent diabetes mellitus was very uncommon. An amino acid sequence in the catalytic site of HIV protease was found to have a significant homology with a low density lipoprotein receptor-like protein. These results tend to implicate the protease inhibitors themselves in the development of this problem.

However, other researchers have found that the protease inhibitors per se are not always associated with the morphologic and metabolic abnormalities of lipodystrophy syndrome and HADDS (Lo et al, 1998; Kotler et al, 1998; Brinkman 1999; Carr, 1999b; Gervasconi, 1999; Hadigan et al, 1999). Morphologic and metabolic changes are not seen consistently in all protease inhibitor-treated patients, and many patients have only certain elements of the syndrome. In some cases the abnormal morphologic and/or metabolic manifestations have been observed in patients who have never received any type of antiretroviral medication (Lo et al, 1998; Carr et al, 1998a, 1998b, 1999a, 1999b; Mercie et al, 1999).

Even though HIV patients with visceral adiposity and buffalo hump have phenotypes that are reminiscent of Cushing's syndrome, it is unlikely that HADDS patients will have Cushing's syndrome. In a case series of HIV patients with buffalo hump, Lo et al (1998) found that fasting serum cortisol concentrations and standard dexamethasone suppression tests were normal. In a case series of HIV patients with abnormal visceral adipose tissue accumulation (Kotler et al, 1998), and in one of the patients of with buffalo hump (Lo et al, 1998) moderate elevations in 24-hour urinary-free cortisol were observed. However, even though there may be subtle abnormalities in cortisol in patients with HADDS, so far Cushing's syndrome has been ruled out in all of them by the standard dexamethasone suppression test.

As mentioned above, the possibility of concomitant AIDS wasting and/or depletion of lean body mass a consideration in HADDS. Despite advances in treating the retrovirus infection and the complications of AIDS, some HIV-infected patients still develop overt AIDS wasting (or cachexia), which involves profound depletion of weight and lean body mass. Overt AIDS wasting, defined as an involuntary weight loss exceeding 10% of usual body weight, has become less prevalent since the widespread use of highly active antiretroviral therapy, and probably occurs in fewer than 10% of patients receiving highly active antiretroviral therapy (Mocroft, 1999). Similarly, in one large case series, fewer than 10% of HADDS patients exhibited overt AIDS wasting (Muurahainen et al, unpublished observations).

However, HIV patients may also present with "occult wasting", defined as a significant depletion of lean body mass without significant weight loss (Muurahainen, 1994). The prevalence of occult wasting in patients with HADDS is currently under investigation. Since occult wasting may occur in patients receiving combination antiretroviral therapy (Muurahainen, 1994; Gibert, 1996), it is possible that patients with HADDS will also display depletion of lean body mass without weight loss, or occult wasting.

To summarize, HADDS is newly discovered a HIV-related syndrome involving relatively rapid, pathologic accumulation of adipose tissue in specific depots that develops over a period of several months to years, frequently in association with subcutaneous peripheral lipodystrophy (facial and limb wasting), and occasionally associated with hyperlipidemia and hyperinsulinemia, in the absence of hypercortisolism. The syndrome may also be associated with other physiological changes such as premature atherosclerosis, depletion of lean body mass, and other physiologic abnormities. As such, HADDS is a unique clinical entity in the history of medicine.

With respect to the invention described herein, it should be noted that a small percentage (probably fewer than ten percent) of HADDS patients in the United States have overt AIDS wasting (Muurahainen et al, unpublished observations, Serono Laboratories, Inc), although in probably more, if not all HADDS patients, occult wasting may be present. It should be noted that many patients with overt AIDS wasting are able to tolerate relatively high doses (6 mg/day) of recombinant growth hormone (rhGH; Serono's SEROTSIM) administered subcutaneously (s.c.), without developing adverse effects that require dose reduction or cessation of therapy (Schambelan et al, 1996).

In comparison to AIDS wasting patients, healthy (non-HIV infected, non-wasting) adults, when given 6 mg/day s.c. injections of rhGH will probably develop more symptomatology such as tissue turgor, joint stiffness, arthalgias, and/or paresthesias necessitating dose reduction or cessation of therapy (data on file, Serono Laboratories, Inc/, Norwell, Mass.). Dose-ranging trials are currently being designed to investigate the most effective and safe doses of rhGH for patients with HADDS, and to ascertain whether HADDS patients with occult and overt wasting are able to tolerate higher doses than HADDS patients without overt or occult wasting, if any.

Also with respect to the invention proposed herein, it should be noted that Bjorntorp and others (1996) have reported a disease entity termed metabolic syndrome X (or syndrome X), occurring in non-HIV-infected adults, that bears several similarities to HADDS. Patients with syndrome X typically present with mild to moderate visceral truncal adiposity, hyperlipidemia, insulin resistance, sometimes diabetes and hypertension, and occasionally associated with signs of premature atherosclerosis. However, this non-HIV related syndrome typically develops over many years. Moreover, compared to HADDS, syndrome X is not typically associated with (1) chronic HIV infection (2) excessive accumulation of adipose tissue in the visceral, dorsocervical, submandibular, supraclavicular, pectoral and/or mammary areas, (3) occasionally profound lipodystrophy or lipoatrophy of subcutaneous fat in the face, arms, legs, and/or buttocks, (4) lipomas, either multiple or single (if any at all), and (5) wasting, either overt or occult.

Other than for the invention proposed below, there is no currently known medical therapy that effectively treats the primary pathological abnormality of HADDS. Of course, there are a few approaches to the treatment of several abnormalities occasionally observed in patients with HADDS, such as hyperlipidemia, hyperinsulinemia/diabetes, wasting/cachexia, pancreatitis, gout, and hypogonadism. Sometimes these conditions can be managed in HADDS patients almost exactly as managed in non-HIV-infected patients.

However, the potential for reduction of the abnormal adipose tissue accumulation is uncertain. Since visceral adiposity, buffalo hump, and other fat accumulation in HIV-1-infected individuals with HADDS does not the result from Cushing's Syndrome (Lo et al, 1998), it would be unwise to treat it as such. Dietary modification and exercise are of limited success in reducing abnormally distributed regional fat accumulation such as buffalo hump and visceral adiposity (Kotler et al, personal communication). As described above, antiretroviral switch strategies have been disappointing at best. Saint-Marc (1999) has reported that the antihyperglycemic agent metformin may result in reduced total, subcutaneous, and visceral fat. However, because of its adverse effect profile, metformin may not be the best therapeutic agent to offer to most patients with HADDS.

Surgical interventions, such as liposuction and surgical excision, have been used with limited success to treat abnormally accumulated adipose tissue in the dorsocervical, submandibular, breast areas, or as lipomas. It is not feasible to liposuction abnormally accumulated visceral adipose tissue due to the risk of bowel perforation. Liposuction or plastic surgery produce only temporary relief, because the abnormal fat typical re-accumulates following surgical excision. Repeat surgical procedures augment risks of anesthesia and scarring. Moreover, the surgical techniques do not affect the metabolic abnormalities sometimes associated with HADDS.

SEROSTIM®, recombinant human growth hormone (rhGH) produced by Serono Laboratories, Inc., has recently been given accelerated FDA approval for treating wasting syndrome in patients with AIDS or AIDS-related cachexia.

Windisch et al (1998) reported that AIDS-associated wasting was characterized by weight loss, depletion of lean body mass and preservation of body fat, leading to muscle weakness and organ failure. Although the FDA has approved recombinant growth hormone for treating AIDS-associated wasting, the adverse event profile is similar to that of other recombinant growth hormone products. Trials of recombinant growth hormone on the control of wasting in patients with AIDS have been encouraging. Post-marketing experience with over 10,000 AIDS wasting patients receiving SEROSTIM® since 1996 reveals that a three-month course of therapy was effective in the majority of patients with AIDS wasting.

Krentz et al (1993) compared metabolic and anthropometric changes induced by recombinant human growth hormone dosed at 5.0 versus 2.5 mg every other day (qod) in 10 patients with HIV/AIDS. During treatment, insulin-like growth factor-1 (IGF-1) levels increased significantly in the pharmacological rhGH treatment group receiving 5.0 mg qod, whereas no significant change was observed in IGF-1 in the group receiving 2.5 mg qod of rhGH. In the group treated with 5.0 mg qod dose of hGH, weight loss preceding the study was reversed in each of the four patients who completed the study. This weight gain was associated with increases in lean body mass and total body water, and with concomitant decreases in fat mass and urinary nitrogen excretion.

In a large, randomized, placebo-controlled study, Schambelan et al (1996) used dual X-ray absorptiometery (DXA) scanning to evaluate changes in body composition produced by administration of recombinant human growth hormone dosed at 0.1 mg/kg/day (or 4 to 6 kg per day, depending on patient weight) compared to placebo over a 12 weeks course of therapy. By the end of treatment, significant increases in lean body mass and weight were observed in the rhGH group, compared to the placebo group, and these increases correlated with improvements in physical function (treadmill performance). The rhGH therapy was associated with minor increments in fasting plasma glucose, which were of negligible clinical significance.

SUMMARY OF THE INVENTION

It is an object of the present invention to overcome the aforementioned deficiencies in the prior art.

It is another object of the present invention to treat any type of HADDS and related syndromes, including excess accumulation of adipose tissue in the visceral, submandibular, supraclavicular, dorsocervical, pectoral, and/or mammary areas, as well as subcutaneous lipomas (which may occur singly or multiply), with recombinant human growth hormone (rhGH) or any other substance which binds to and initiates signalling of the human growth hormone receptor or which stimulates release of or potentiates the activity of endogenous hGH.

According to the present invention, human growth hormone (hGH) is administered to treat HADDS and possibly related syndromes, such as metabolic syndrome X (or syndrome X) in patients without HIV infection, or any non-HIV related lipodystrophy syndrome (hereditary or acquired) that includes abnormal adipose tissue accumulation.

Because HIV patients are more likely to have wasting than non-HIV-infected patients, and because patients with wasting appear better able to tolerate supraphysiologic doses of rhGH than non-wasting patients, it is postulated that, if supraphysiologic doses of rhGH are required to reduce abnormally accumulated adipose tissue, the therapy will be better tolerated by patients with HADDS than non-HIV-infected patients with related syndromes. Nevertheless, in one embodiment of the present invention, the treatment is only directed to HADDS patients who do not present with AIDS wasting.

The human growth hormone administered is preferably recombinant human growth hormone (rhGH). Alternatively, a substance which stimulates release of endogenous growth hormone, such as growth hormone releasing hormone (GHRH) or other substances which agonize the GHRH receptor, may be used. Any HADDS patient can be treated by means of the present invention.

DETAILED DESCRIPTION OF THE PRESENT INVENTION

The present invention relates to the discovery that HIV-associated dysmorphia/dysmetabolic syndrome (HADDS) may be treated by the administration of an effective amount of human growth hormone. The HADDS which may be treated in accordance with the present invention may present itself as, for example, dorsocervical fat pads ("buffalo hump"), visceral adiposity ("truncal obesity", "omental fat accumulation", "Crix belly" or "protease paunch"), abnormal pectoral or mammary fat accumulation, and other abnormal fat accumulation in other depots (including submandibular fat accumulation or "horse collar", and lipomas, either single, multiple, or bilateral symmetric lipomatoses).

Human growth hormone, also known as somatotropin, is a protein hormone produced and secreted by the somatotropic cells of the anterior pituitary. Secretion is regulated by a releasing factor, i.e., the growth hormone-releasing hormone (GHRH), and by an inhibitory factor, somatostatin. Human growth hormone plays a key role in somatic growth through its effects on the metabolism of proteins, carbohydrates and lipids.

Human growth hormone is a single polypeptide chain of 191 amino acids (Bewley et al, 1972) having two disulfide bonds, one between Cys-53 and Cys-165, forming a large loop in the molecule, and the other between Cys-182 and Cys-189, forming a small loop near the C-terminus. The DNA sequence that confirmed the amino acid sequence was reported by Martial et al (1979). Purified hGH is a white amorphous powder in its lyophilized form. It is readily soluble (concentrations >10 mg/L) in dilute aqueous buffers at pH greater than 7.2.

In solution, hGH exists predominantly as a monomer, with a small fraction as dimers and higher molecular weight oligomers. Under certain conditions, hGH can be induced to form larger amounts of dimers, trimers and higher oligomers.

Several derivatives of hGH are known, including naturally-occurring derivatives, variants and metabolic products, degradation products primarily of biosynthetic hGH and engineered derivatives of hGH produced by genetic methods. One example of a naturally-occurring derivative of hGH is GH-V, a variant of growth hormone found in the placenta. Other members of the gene locus are described in Chen et al (1989). Any derivative of hGH, including derivatives designed to be long-lasting in the body, can be used for the purpose of the present invention as long as it retains the biological activity of hGH.

Methionyl hGH was the first form of hGH to be produced through recombinant DNA technology. This compound is actually a derivative of hGH having one additional methionine residue at its N-terminus (Goeddel et al, 1979).

A naturally-occurring variant of hGH called 20-K-hGH has been reported to occur in the pituitary as well as in the bloodstream (Lewis et al, 1978; Lewis et al, 1980). This compound, which lacks the 15 amino acid residues from Glu-32 to Gln-46, arises from an alternative splicing of the messenger ribonucleic acid (DeNoto et al, 1981). This compound shares many, but not all of the biological properties of hGH.

20-K-HGH is made in the pituitary and secreted into the blood. It makes up about 5% of growth hormone output of adults, and about 20% of growth hormone output of children. It has the same growth promoting activity as 22 kD growth hormone, and has been reported to have equal to or greater the amount of lipolytic activity as the 22 kD form. It binds to growth hormone receptors with equal affinity as the 22 kD growth hormone, and has one tenth the lactogenic (prolactin-like) bioactivity as the 22 kD hormone. Unlike 22 kD, the 2-k-HGH has weak anti-insulin activity.

A number of derivatives of hGH arise from proteolytic modifications of the molecule. The primary pathway for the metabolism of hGH involves proteolysis. The region of hGH around residues 130–150 is extremely susceptible to proteolysis, and several derivatives of hGH having nicks or deletions in this region have been described (Thorlacius-Ussing, 1987). This region is in the large loop of hGH, and cleavage of a peptide bond there results in the generation of two chains that are connected through the disulfide bond at Cys-53 and Cys-165. Many of these two-chain forms are reported to have increased biological activity (Singh et al, 1974). Many derivatives of human growth hormone have been generated artificially through the use of enzymes. The enzymes trypsin and subtilisin, as well as others, have been used to modify hGH at various points throughout the molecule (Lewis et al, 1977b; Graff et al, 1982). One such derivative, called two-chain anabolic protein (2-CAP), was formed through the controlled proteolysis of hGH using trypsin (Becker et al, 1989). 2-CAP was found to have biological properties very distinct from those of the intact hGH molecule, in that the growth-promoting activity of hGH was largely retained and most of the effects on carbohydrate metabolism were abolished.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, 1981). Deamidated hGH has been shown to have an altered susceptibility to proteolysis with the enzyme subtilisin, suggesting that deamidation may have physiological significance in directing proteolytic cleavage of hGH. Biosynthetic hGH is known to degrade under certain storage conditions, resulting in deamidation at a different asparagine (Asn-149). This is the primary site of deamidation, but deamidation at Asn-152 is also seen (Becker et al, 1988). Deamidation at Gln-137 has not been reported in biosynthetic hGH.

Methionine residues in proteins are susceptible to oxidation, primarily to the sulfoxide. Both pituitary-derived and biosynthetic hGH undergo sulfoxidations at Met-14 and Met-125 (Becker et al, 1988). Oxidation at Met-170 has also been reported in pituitary but not biosynthetic hGH. Both desamide hGH and Met14 sulfoxide hGH have been found to exhibit full biological activity (Becker et al, 1988).

Truncated forms of hGH have been produced, either through the actions of enzymes or by genetic methods. 2-CAP, generated by the controlled actions of trypsin, has the first eight residues at the N-terminus of hGH removed. Other truncated versions of hGH have been produced by modifying the gene prior to expression in a suitable host. The first 13 residues have been removed to yield a derivative having distinctive biological properties (Gertler et al, 1986) in which the polypeptide chain is not cleaved.

Although human growth hormone was originally obtained from pituitary glands of cadavers, these preparations were not electorphoretically homogeneous, and antibodies appeared in the serum of patients treated with preparations of the order of 50% purity, the immunogenicity being attributed to inactive components. Recombinant DNA technology permitted production of an unlimited supply of hGH in a number of different systems. Purification of hGH from the culture medium is facilitated by the presence of only low amounts of contaminating proteins. In fact, it has been shown that hGH can be purified on a laboratory scale by a single purification step on a reversed-phase HPLC column (Hsiung et al, 1989).

Recombinant human growth hormone, rhGH, is produced by Serono Laboratories, Inc., as SEROSTIM®, which product has been given accelerated FDA approval for treating weight loss and wasting in AIDS patients. PROTROPIN®, produced by Genentech, Inc. (South San Francisco, Calif.), differs slightly in structure from natural sequence hGH, having an additional methionine residue at the N-terminus. Recombinant hGH is generally marketed as vials containing hGH plus additional excipients, e.g., glycine and mannitol, in a lyophilized form. A companion diluent vial is provided, allowing the patient to reconstitute the product to the desired concentration prior to administration of the dose. Recombinant hGH can also be marketed in other well-known manners, such as prefilled syringes, etc.

After intravenous administration, the elimination of hGH is described by first-order kinetics with a serum half-life of 1230 minutes in both animals and humans (Moore et al, 1988; Hendricks et al, 1985). Traditionally, intramuscular injection has been the method of choice as the preferred route of delivery. In humans, absorption of exogenous hGH appears to be more rapid from the intramuscular site, with a time to maximum concentration of two to three hours, compared to four to six hours after subcutaneous administration. The disappearance phase from serum has been reported to range from 12–20 hours for intramuscular administration, and 20–24 hours after subcutaneous administration (Albertsson-Wikland et al, 1986; Jorgensen et al, 1987). In general, no significant differences have been observed in the pharmacokinetics or biological activities of recombinant natural sequence hGH, recombinant N-methionyl-hGH, or pituitary-derived material in humans (Moore et al, 1988; Jorgensen et al, 1988).

The term "human growth hormone", as used in the present invention, is intended to include the naturally-occurring derivatives, as noted above, including, without limitation, both the 20 kD and the 22 kD human growth hormone, GH-V, and other members of the growth hormone gene locus as described in Chen et al (1989). The term also includes functional derivatives, fragments, variants, analogs, or salts which retain the biological activity of growth hormone, i.e., which act as agonists to the growth hormone receptor. In other words, they are capable of binding to the growth hormone receptor to initiate the signaling activity of the receptor.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of hGH as described herein, i.e., the ability to bind the hGH receptor and initiate receptor signalling, and do not confer toxic properties on compositions containing it. Derivatives may have chemical moieties, such as carbohydrate or phosphate residues, provided such a derivative retains the biological activity of hGH and remains pharmaceutically acceptable.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the molecule in body fluids.

Of particular importance is a growth hormone that has been derivatized or combined with a completing agent to be long lasting. For example, pegylated versions, or growth hormones genetically engineered to exhibit long lasting activity in the body, can be used to treat HADDS according to the present invention.

HGH that is acetylated at the N-terminus has been isolated and identified (Lewis et al, 1979). It is not clear if acylation serves a regulatory role or is simply an artifact of the purification. However, it is expected that this the molecule exhibits anti-HADDS activity in a similar fashion to other hGH derivatives.

The term "derivatives" is intended to include only those derivatives that do not change one amino acid to another of the twenty commonly-occurring natural amino acids.

The term "salts" herein refers to both salts of carboxyl groups and to acid addition salts of amino groups of the hGH molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of hGH relevant to the present invention, i.e., the ability to bind to the hGH receptor and initiate receptor signalling.

A "fragment" of the growth hormone according to the present invention refers to any subset of the molecule, that is, a shorter peptide which retains the desired biological activity. Fragments may readily be prepared by removing amino acids from either end of the hGH molecule and testing the resultant for its properties as an hGH receptor agonist. Proteases for removing one amino acid at a time from either the N-terminal or the C-terminal of a polypeptide are known, and so determining fragments which retain the desired biological activity involves only routine experimentation.

Additionally, the polypeptide which has such hGH receptor agonist activity, be it hGH, an analog or variant, salt, functional derivative or fragment thereof, can also contain additional amino acid residues flanking the hGH polypeptide. As long as the resultant molecule retains the hGH receptor agonist ability of the core polypeptide, one can determine whether any such flanking residues affect the basic and novel characteristics of the core peptide, i.e., its receptor agonist characteristics, by routine experimentation. The term "consisting essentially of", when referring to a specified sequence, means that additional flanking residues can be present which do not affect the basic and novel characteristic of the specified sequence. This term does not comprehend substitutions, deletions or additions within the specified sequence.

A "variant" of the human growth hormone according to the present invention refers to a molecule which is substantially similar to either the entire peptide or a fragment thereof. Variant peptides may be conveniently prepared by direct chemical synthesis of the variant peptide, using methods well known in the art. Of course, a variant human growth hormone would have similar similar hGH receptor binding and signal initiating activity as hGH and which would, therefore, be expected to have similar anti-HADDS activity to hGH.

Amino acid sequence variants of the human growth hormone can be prepared by mutations in the DNAs which encode the synthesized human growth hormone derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (cf. European Patent Publication No. EP 75,444, the entire contents of which being hereby incorporated by reference).

At the genetic level, these variants ordinarily are prepared by site-directed autogenesis (as exemplified by Adelman et al, 1983) of nucleotides in the DNA encoding the peptide molecule, thereby producing DNA encoding the variant, and thereafter expressing the DNA in recombinant cell culture. The variants typically exhibit the same qualitative biological activity as the non-variant peptide.

An "analog" of human growth hormone according to the present invention refers to a non-natural molecule which is substantially similar to either the entire molecule or to an active fragment thereof. An analog of human growth hormone useful in the present invention would exhibit anti-HADDS activity.

The types of substitutions which may be made in the human growth hormone according to the present invention may be based on analysis of the frequencies of amino acid changes between a homologous protein of different species. Based upon such analysis, conservative substitutions may be defined herein as exchanges within one of the following five groups:

I. Small, aliphatic, nonpolar or slightly polar residues:
Ala, Ser, Thr, Pro, Gly II. Polar, negatively-charged residues and their amides:
Asp, Asn, Glu, Gln III. Polar, positively-charged residues:
His, Arg, Lys IV. Large, aliphatic non-polar residues:
Met, Leu, Ile, Val, Cys V. Large aromatic residues:
Phe, Try, Trp Within the foregoing groups, the following substitutions are considered to be "highly conservative":

Asp/Glu
His/Arg/Lys
Phe/Tyr/Trp
Met/Leu/Ile/Val

Semi-conservative substitutions are defined to be exchanges between two of groups (I)–(IV) above which are limited to supergroup (A), comprising (I), (II), and (III) above, or to supergroup (B), comprising (IV) and (V) above. Substitutions are not limited to the genetically encoded or even the naturally occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5imidazoyl) propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide is also useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; 0-methyliosurea; 2,4-pentanedione; and transaminase-catalyzed reaction with glyoxylate.

Arginyl residues are modified by reaction with one or several conventional reagents, among them phenylglyoxal; 2,3butanedione; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and e-nitro derivatives, respectively.

Carboxyl side groups (aspartyl or glutamyl) are selectively modified by reaction with carbodiimides (R'N—C—N—R'), such as 1-cyclohexyl-3-[2-morpholinyl-(4-ethyl)] carbodiimide or 1 ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Examples of production of amino acid substitutions in proteins which can be used for obtaining analogs of the hGH for use in the present invention include any known method steps, such as presented in U.S. Pat. Nos. RE 33,653; 4,959,314; 4,588,585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al).

Among the substances which bind to and initiate signalling of the human growth hormone receptor which may be used in accordance with the present invention are all of those growth hormone analogs and mimetics already known in the literature, such as, for example, are disclosed in U.S. Pat. Nos. 5,851,992; 5,849,704; 5,849,700; 5,849,535; 5,843,453; 5,834,598; 5,688,666; 5,654,010; 5,635,604; 5,633,352; 5,597,709; and 5,534,617.

Preferably, the hGH variant or analog will have a core sequence, which is the same as that of the native sequence or biologically active fragment thereof, which has an amino acid sequence having at least 70% identity to the native amino acid sequence and retains the biological activity thereof. More preferably, such a sequence has at least 80% identity, at least 90% identity, or most preferably at least 95% identity to the native sequence.

The term "sequence identity" as used herein means that the sequences are compared as follows. The sequences are aligned using Version 9 of the Genetic Computing Group's GAP (global alignment program), using the default (BLOSUM62) matrix (values −4 to +11) with a gap open penalty of −12 (for the first null of a gap) and a gap extension penalty of −4 (per each additional consecutive null in the gap). After alignment, percentage identity is calculated by expressing the number of matches as a percentage of the number of amino acids in the claimed sequence.

Analogs or variants in accordance with the present invention may also be determined in accordance with the following procedure. The DNA of the native sequence is known to the prior art and is found in the literature (Martial et al, 1979). Polypeptides encoded by any nucleic acid, such as DNA or RNA, which hybridizes to the complement of the native DNA or RNA under highly stringent or moderately stringent conditions, as long as that polypeptide maintains the biological activity of the native sequence, are also considered to be within the scope of the present invention.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm = 81.5° C. + 16.6(\text{Log } M) + 0.41(\% \text{ GC}) - 0.61(\% \text{ form}) - 500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to equation of Meinkoth, hybridization will occur even if there is up to about 10% mismatch.

As used herein, highly stringent conditions are those which are tolerant of up to about 15% sequence divergence, while moderately stringent conditions are those which are tolerant of up to about 20% sequence divergence. Without limitation, examples of highly stringent (12–15° C. below the calculated Tm of the hybrid) and moderately (15–20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 µg/ml denatured, fragmented salmon sperm DNA at a temperature approximately 20° to 25° C. below the Tm. If mixed probes are used, it is preferable to use tetramethyl ammonium chloride (TMAC) instead of SSC (Ausubel, 1987–1998).

While the present invention provides recombinant methods for making the human growth hormone derivatives, these derivatives may also be made by conventional protein synthesis methods which are well known to those skilled in the art.

The growth hormone treatment in accordance with the present invention may be accomplished either by administration of exogenous growth hormone or by administration of a substance which stimulates production of endogenous growth hormone either directly or indirectly by supressing endogenous somatostatin secretion. It is known that human growth hormone releasing hormone (hGHRH) stimulates the release of hGH. Thus, the biological activity of hGH can be indirectly obtained by administering GHRH or a functional derivative, salt, variant, analog or fragment thereof which retains the biological activity of GHRH, i.e., the ability to stimulate the release of growth hormone. Thus, for example, besides GHRH there may be used functional derivatives thereof in accordance with the above definition, analogs or variants thereof, which have at least 70% sequence identity, more preferably 80% or 90% or, most preferably, 95% sequence identity therewith, yet retains the biological activity of GHRH, or a variant or analog which is a polypeptide encoded by a DNA which hybridizes to the native DNA encoding GHRH under moderately stringent conditions, or preferably under highly stringent conditions, all in accordance with the definitions given hereinabove. Any of the GHRH or GHRH analogs or agonists known in the literature and disclosed as simulating the release of growth hormone can be used in the present invention, such as those disclosed in U.S. Pat. Nos. 5,792,747; 5,776,901; 5,696,089; 5,137,872; 5,767,085; 5,612,470; 5,846,936; and 5,847,066. See also Thorner et al (1997), Felix et al (1995), Alba-Roth et al (1988), Friend et al (1997).

Other substances capable of promoting the release of growth hormone in vivo which can be used in accordance with the present invention include those disclosed in U.S. Pat. Nos. 5,807,985; 5,804,578; 5,795,957; 5,777,112; 5,767,118; 5,731,317; 5,726,319; 5,726,307; 5,721,251; 5,721,250, etc.

There can also be used in accordance with the present invention any other molecule which binds to the hGH receptor and initiates signalling of that receptor. It is known, for example, that small molecules, sometimes called secretagogues, have been developed which bind hGH receptors and cause them to aggregate and initiate signalling, which signal initiation is the same as one obtains with natural hGH binding to the receptor. Such molecules are known, for example, from U.S. Pat. Nos. 5,773,441; 5,798,337; 5,830,433; 5,767,124; and 5,723,616. See also Bowers et al (1991), Thorner et al (1997), Camanni et al (1998), Ankersen et al (1998), Smith et al (1993) and Ghigo et al (1998). Thus, the present invention is intended to include any substance which binds to hGH receptor and initiates signalling thereof so as to obtain the same ultimate qualitative effect as the administration of natural hGH, insofar as the treatment of HADDS is concerned.

Pharmaceutical compositions for administration according to the present invention can comprise at least one human growth hormone according to the present invention in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art for treating HADDS.

For example, administration can be by parenteral, such as subcutaneous, intravenous, intramuscular, intraperitoneal, aerosol, or trahsdermal routes. The dosage administered depends upon the age, health and weight of the recipient, type of previous or concurrent treatment, if any, frequency of the treatment and the nature of the effect desired.

Compositions within the scope of this invention include all compositions comprising at least one human growth hormone or derivative, analog, or variant thereof according to the present invention in an amount effective to achieve its intended purpose. While individual needs vary, determination of optimal ranges of effective amounts of each component is within the skill of the art. Typical dosages comprise about 0.01 to about 0.1 mg/kg body weight per day, which will usually amount to about 1–6 mg/day, subcutaneously for 5–30 weeks. When administered to AIDS patients, the hGH anti-HADDS therapy may be administered concomitantly with other AIDS therapies. Since supraphysiologic doses of hGH (>5 mg/day) have been safely administered to AIDS wasting patients continuously on a daily basis as s.c. injections for periods of two to four years (data on file, Serono Laboratories, Inc), in HADDS patients in whom the abnormal adipose tissue re-accumulates, re-treatment or maintenance therapies will be considered.

It should also be understood that, to be useful, the treatment provided need not be absolute, provided that it is sufficient to carry clinical value. An agent which provides treatment to a lesser degree than do competitive agents may still be of value if the other agents are ineffective for a particular individual, if it can be used in combination with other agents to enhance the overall level of protection, or if it is safer than competitive agents.

It is understood that the suitable dose of a composition according to the present invention will depend upon the age, health and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This typically involves adjustment of a standard dose, e.g., reduction of the dose if the patient has a low body weight.

The total dose required for each treatment may be administered in multiple doses or in a single dose. The compositions may be administered alone or in conjunction with other therapeutics directed to the disease or directed to other symptoms thereof.

In addition to the compounds of the invention, a pharmaceutical composition may contain suitable pharmaceutically acceptable carriers, such as excipients, carriers and/or auxiliaries which facilitate processing of the active compounds into preparations which can be used pharmaceutically.

EXPERIMENTAL

Eight AIDS patients, six male and two female, with a history of long-term use (an average of 12 months) of highly active antiretroviral therapy (HAART), including protease inhibitors (6 indinavir, 2 ritonavir/saquinavir) developed HADDS, including buffalo humps, central adiposity and peripheral muscle wasting associated with fatigue, along with elevated levels of plasma triglycerides +/- cholesterol.

Therapy with rhGH (SEROSTIMw,w) was initiated in all patients at a dose of 6 mg/day subcutaneously. Four patients completed three months of rhGH and had notable improvements in fat maldistribution, with 25–75% reduction in buffalo hump syndrome and abdominal girth, but no change in peripheral lipodystrophy. Weights were stable, and there were no consistent changes in total body fat and blood lipids, despite 5–10% gain in fat-free mass. One patient discontinued rhGH due to carpal tunnel syndrome and had recurrence of HADDS. Three patients have had over six months of therapy. One patient was lost to follow-up after six weeks of therapy, and one patient has received fewer than eight weeks of therapy. Yet, at last observation, all had notable reductions in the size of and firmness of the buffalo hump and truncal adiposity. These experiments establish that rhGH is effective in treating HADDS, including reduction of buffalo humps and truncal adiposity.

Since the time that this invention was initially reported, these findings have been replicated in over 40 HIV patients with HADDS (Torres et al, 1998; Torres, 1999; Wanke et al, 1999; Mauss et al, 1999; Engleson et al 1999; Milano et al, 1999). Torres (1999) has reported that, by four months, rhGH therapy dosed at 4 to 6 mg/day significantly reduces the size and firmness of buffalo humps, and reduces truncal adiposity, with no change in peripheral lipodystrophy, while fat free mass increased 5 to 10%. There were no significant or consistent changes in body weight, total body fat, or blood lipids during the treatment period.

Collectively, these clinical studies cited above demonstrate that therapy with rhGH (SEROSTIM®), administered subcutaneously, in doses ranging from 3 to 6 mg per day for 12 to 24 weeks significantly reduces abnormally accumulated fat, compared to baseline. Specifically, SEROSTIM® (rhGH) has been shown to reduce abdominal girth (Wanke et al, 1999), visceral adiposity (Engelson et al, 1999, Mauss et al,1999), buffalo hump (Torres, 1998, 1999), and solitary lipomas (Milano et al, 1999). Therapy with rhGH (SEROSTIM®) also increased lean body mass and body cell mass as quantified by bioelectrical impedance analysis (Wanke et al, 1999; Engelson et al, 1999).

Collective side effects included swelling of the fingers or paresthesia due to tissue turgor, a few transient elevations of fasting glucose and triglycerides. At 12 weeks, total cholesterol and fasting triglycerides dropped significantly, while HDL cholesterol and glucose increased, but none of these changes were deemed clinically significant (Engelson et al, 1999). No additional episodes of hypertension or elevated pancreatic enzymes have been reported.

As noted earlier, additional prospective, randomized, double-blind, placebo-controlled dose-ranging studies are underway to ascertain the most optimally safe and effective dose of SEROSTIM® (rhGH), duration of treatment, and requirements for periodic re-treatment and/or maintenance therapy (if any) needed to sustain the reduction of abnormally accumulated fat. Other clinical endpoints such as the effects of SEROTSIM on different adipose tissue depots, lipoprotein profile, insulin sensitivity, early atherosclerotic lesions will also be investigated.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Adelman et al, "In vitro deletional mutagenesis for bacterial production of the 20,000-dalton form of human pituitary growth hormone", *DNA* 2(3):183–193 (1983)

Albertsson-Wikland et al, "Daily subcutaneous administration of human growth hormone in growth hormone deficient children", *Acta Paediatr Scand* 75(1):89–97 (1986)

Becker et al, Biotechnology 5:499 (1987)

Becker et al, "Isolation and characterization of a sulfoxide and a desamido derivative of biosynthetic human growth hormone" *Biotechnol Appl Biochem* 10(4):326–337 (1988)

Becker et al, Abstract. No. 342, 71st Annual Meeting, The Endocrine Society, Seattle, Wash., June 1989.

Bewley et al, "Sequence comparison of human pituitary growth hormone, human chorionic somatomammotropin, and ovine pituitary growth and lactogenic hormones" *Int J Pept Protein Res* 4(4):281–287 (1972)

Bewley et al, "The chemistry of human pituitary growth hormone", *Adv Enzymol Relat Areas Mol Biol* 42:73–166 (1975)

Bjorntorp P, "The regulation of adipose tissue distribution in humans" *Int J Obes Relat Metab Disord* 20(4):291–302 (1996)

Bjorntorp P, "Abdominal obesity and the development of noninsulin dependent diabetes mellitus", *Diabetes Metab Rev* 4:615–622 (1998) (cited in Kotler 1999 JAIDS)

Brinkman K, "Mitochondrial toxicity of nucleoside analogue reverse transcriptase inhibitors", *Antiviral Therapy*; 4: (Sup 2):15 [Abstract 009] (1999)

Carr et al, "A syndrome of peripheral lipodystrophy and insulin resistance in patients receiving HIV protease inhibitors", *AIDS* 12:F51–58 (1998a)

Carr et al, "Pathogenesis of HIV-1 protease inhibitor-associated peripheral lipodystrophy, hyperlipidemia, and insulin resistance", *Lancet* 131:1881–1883 (1998b)

Carr et al, "Diagnosis, prediction, and natural course of HIV-1 protease-inhibitor-associated lipodystrophy, hyperlipidaemia, and diabetes mellitus: a cohort study", *Lancet* 353(9170):2093–2099 (1999a)

Carr et al, "A syndrome of lipodystrophy (LD), lactic acidemia and liver dysfunction associated with HIV nucleoside analogue reverse transcriptase inhibitor therapy: contribution to PI-related LD syndrome", *Antiviral Therapy* 4(Sup 2):19 [Abstract 11] (1999b)

Cheng B, "Lipodystrophy in HIV: a community perspective", *Antiviral Therapy*; 4(Sup 2):19 [Abstract 10] (1999)

Chen et al, "The human growth hormone locus: nucleotide sequence, biology, and evolution", *Genomics* 4(4): 479–497 (1989)

Cunningham et al, "Dimerization of human growth hormone by zinc", *Science* 253(5019):545–548 (1991)

DeNoto, "Human growth hormone DNA sequence and mRNA structure:possible alternative splicing", *Nucleic Acids Res* 9(15):3719–3730 (1981)

Dong, B J et al, "Diabetes and use of protease inhibitors" 12$^{th}$ World Aids Conference, Geneva (1998) [Abstract 12308]

Dong, K et al, "Changes in body habitus in HIV+ women after initiation of protease inhibitor therapy" 12$^{th}$ World Aids Conference, Geneva (1998) [Abstract 12373]

Engleson et al, "Alterations in body distribution in HIV infection: Regional body composition by whole body MRI and DXA scans" 12$^{th}$ World Aids Conference, Geneva [Abstract 32181] (1998)

Engelson et al, "Effect of recombinant human growth hormone in the treatment of visceral fat accumulation in HIV infection: interim analysis", *Antiviral Therapy* 4:(Sup 2):11 [Abstract 006] (1999a)

Engelson et al, "Fat distribution in HIV-infected patients reporting truncal enlargement quantified by whole-body magnetic resonance imaging", *Am J Clin Nutr* 69(6): 1162–1169 (1999b)

Falutz et al, "Considerations in the development of a case definition for HIV/HAART-associated-lipodystrophy syndrome", *Antiviral Therapy* 4(Sup 2):29 [Abstract 021] (1999)

Food and Drug Administration, "Reports of diabetes and hyperglycemia in patients receiving protease inhibitors for the treatment of human immunodeficiency virus (HIV)", *FDA Public Advisory* (Jun. 11, 1997)

Forum for HIV Collaborative Research (FHCR) Metabolic Abnormalities in HIV Disease and Treatment (April, 1999) www.gwumc.edu/chpr, HIV research Gatell et al, "One year effects of switching from NIV-1 PIs to nevirapine on metabolic abnormalities", *Antiviral Therapy* 4(Supp 2):40 [Abstract 040] (1999)

Gertler et al, "Inhibition of lactogenic activities of ovine prolactin and human growth hormone (hGH) by a novel form of a modified recombinant hGH", *Endocrinology* 72118(2):720–6 (1986)

Gervasconi et al, "Redistribution of body fat in HIV-infected men and women undergoing combination antiretroviral therapy", *AIDS* 134:465–471 (1999)

Gibert et al, "Body cell mass depletion in weight stable HIV patients on protease inhibitors", 12$^{th}$ World AIDS Conference, Geneva (1998)

Goeddel et al, "Direct expression in *Escherichia coli* of a DNA sequence coding for human growth hormone", *Nature* 281(5732):544–548 (1979)

Graff et al, *J Biol Chem* 257:2365 (1982)

Grunfeld C, *J Clin Endo Metab* 74:1045–1052 (1992)

Grunfeld C, "Dyslipidemia due to HIV infection and its therapy", *Antiviral Therapy* 4(Sup 2):7 [Abstract 004] (1999)

Hadigan et al,"Fasting hyperinsulinemia and changes in regional body composition in human immunodeficiency virus-infected women", *J Clin Endocrinol Metab* 84(6): 1932–1937 (1999)

Hendricks et al, "Plasma clearance of intravenously administered pituitary human growth hormone: gel filtration studies of heterogeneous components", *J Clin Endocrinol Metab* 60(5):864–867 (1985)

Henry et al, "Severe premature coronary artery disease with protease inhibitors", *Lancet* 351:1328 (1998a)

Henry et al, "Atorvastatin and gemfibrosil for protease-inhibitor-related lipid abnormalities", *Lancet*; 352:10311032 (1998b)

Hsiung et al, *Biotechnology* 7:267 (1989)

Jones et al, *Biotechnology* 5:499 1987)

Jorgensen et al, "Serum profiles and short-term metabolic effect of pituitary and authentic biosynthetic human growth hormone in man. A double-blind cross-over study", *Acta Endocrinol (Copenh)* 116(3):381–386 (1987)

Jorgensen et al, "Pharmacokinetics of biosynthetic and pituitary human growth hormones in rats", *Pharmacol Toxicol* 63(2):129–134 (1988)

Keruly et al, "Diabetes and hyperglycemia in patients receiving protease inhibitors", 5$^{th}$ Conference on Retroviruses and Opportunistic Infections at Chicago, Ill., (Feb. 1–5, 1998) [ABSTRACT NO. 415]

Kosmiski et al, "An increase in abdominal girth on protease inhibitor therapy is associated with visceral obesity and metabolic disturbances that closely resemble syndrome X", *Antiviral Therapy* 4(Sup 2):49 [Abstract 056] (1999)

Kotler et al, "Alterations in body fat cmposition in HIV-infected men and women", 12$^{th}$ International AIDS Conference, Geneva [Abstract 32173] (1998)

Kotler et al, "Studies of body composition and fat distribution in HIV-infected and control subjects", *J Acquired Immun Defic Syndr.* 20:228–237 (1999)

Kotler and Schambelan, HIV/AIDS 1999 Annual Update, 85–92, hiv.medscape.com (1999)

Krentz et al, "Anthropometric, metabolic, and immunological effects of recombinant human growth hormone in AIDS and AIDS-related complex", *J Acquir Immune Defic Syndr* 6(3):245–251 (1993)

Lewis et al, "An interchain disulfide dimer of human growth hormone", *J Biol Chem* 252(11):3697–3702 (1977a)

Lewis et al, "Enhancement of the hyperglycemic activity of human growth hormone by enzymic modification", *Endocrinology* 101(5):1587–1603 (1977b)

Lewis et al, "A naturally occurring structural variant of human growth hormone", J Biol Chem 25;253(8):2679–2687 (1978)

Lewis et al, "Human growth hormone: additional members of the complex", *Endocrinology* 104(5):1256–1265 (1979)

Lewis et al, "The 20,000-dalton variant of human growth hormone: location of the amino acid deletions", *Biochem Biophys Res Commun* 29;92(2):511–516 (1980)

Lewis et al, "Altered proteolytic cleavage of human growth hormone as a result of deamidation," *J Biol Chem* 25;256(22):11645–11650 (1981)

Lo et al, *The Lancet* 351:867–870 (1998)

Maggi et al, "Precocious lesions of the carotid vessels in HIV-1 infected patients treated with protease inhibitors" *Antiviral Therapy* 4(Sup 2):39 [Abstract 038] (1999)

Martial et al, "Human growth hormone: complementary DNA cloning and expression in bacteria," *Science* 10;205(4406):602–607 (1979)

Mauss et al, "Successful treatment of PI-induced visceral abdominal fat accumulation with R-human growth hormone", *AIDS* 12(Sup 4):145 (1998)

Mercie et al, "Case report of lipodystorophy observations in patients naive of protease inhibitor treatment, Aquitaine Cohort", *Antiviral Therapy* 4(Sup 2):27 [Abstract 018] (1999)

Michael et al, 5$^{th}$ Conference on Retroviruses and Opportunistic Infections, Chicago (February 1998) [Abstract 40]

Milano et al, "Two case reports of unusual lipomatous growths associated with combination antiretroviral therapy" *Antiviral Therapy* 4(Sup 2):41 [Abstract 042] (1999)

Miller et al, "Visceral abdominal-fat accumulation associated with use of indinavir", *Lancet* 21;351(9106):871–875 (1998)

Mocroft et al, "Changes in AIDS-defining illnesses in a London clinic, 1987–1988*", J AIDS* 21:402–407 (1999)

Moore et al, "Equivalent potency and pharmacokinetics of recombinant human growth hormones with or without an N-terminal methionine", *Endocrinology* 122(6):2920–2926 (1988)

Moyle et al, "Changes in visceral adipose tissue and blood lipids in persons reporting fat redistribution syndrome switched from PI therapy to efavirenz",*Antiviral Therapy* 4(Sup 2):48 [Abstract 054] (1999)

Mulligan et al, 5$^{th}$ Conference on Retroviruses and Opportunistic Infections at Chicago, Ill., (Feb. 1–5, 1998) [Abstract No. 41]

Muurahainen et al, "Occult Wasting", 10$^{th}$ World AIDS Conference, Yokohama, Japan [Abstract 32173] (1998)

Muurahainen et al, "The SALSA (self-ascertained lipodystrophy syndrome assessment) cohort: abnormalities in cases compared to controls", *Antiviral Therapy* 4(Sup 2):30 [Abstract 029] (1999a)

Muurahainen et al, "Abnormalities in HIV-associated lipodystrophy syndrome that vary by weight status",*Antiviral Therapy* 4(Sup 2):53 [Abstract 063] (1999b)

Rosenbaum et al, "Prospective follow-up of a PI substitution for efavirenz in patients with HIV-related lipodystrophy syndrome",*Antiviral Therapy* 4(Sup 2):55 [Abstract 068] (1999)

Ruiz et al, "A multicenter, randomized open label comparative trial of the clinical immunological and virological benefits of switching the PI by nevirapine in HAART-experienced patients suffering lipodystrophy", *Antiviral Therapy* 4(Sup 2):35 [Abstract 031] (1999)

Saint-Marc et al, "Reversibility of peripheral fat wasting (lipoatrophy) on stopping staduvine therapy", *Antiviral Therapy* 4(Sup 2):32 [Abstract 024] (1999)

Saint-Marc et al, "Changes in body fat distribution in 154 HIV-infected male patients treated with antiretroviral therapy", *Antiviral Therapy* 4(Sup 2):321 [Abstract 025] (1999)

Saint-Marc, "Effects of metformin on insulin resistance and central adiposity", 6$^{th}$ Conference on Retroviruses and Opoprtunisitic Infections, Chicago, Ill. (February 1998) [Abstract 415]

Schambelan et al, "Recombinant human growth hormone in patients with HIV-associated wasting. A randomized, placebo-controlled trial";. Serostim Study Group, *Ann Intern Med* 125(11):873–882 (1996)

Singh et al, "Modified forms of human growth hormone with increased biological activities", *Endocrinology* 94(3):883–891 (1974)

Stein J H, cited by C W Henderson, Conference News Reports, AIDS Weekly via NewsRx.com (Nov. 22, 1999)

Stolar et al, "Plasma "big" and "big-big" growth hormone (GH) in man: an oligomeric series composed of structurally diverse GH monomers", *J Clin Endocrinol Metab* 59(2):212218 (1984)

Stolar et al, *J Clin Endocrinol Metab* 59:212 (1986)

Struble and Piscitelli, "Syndromes of abnormal fat redistribution and metabolic complications in HIV-infected patients", *Am J Health Syst Pharm* Nov 15;56(22):2343–2348 (1999)

Thiebaut et al, "Lipodystrophy, glucose, and lipid metabolism dysfunctions, Aquitaine Cohort", *Antiviral Therapy* 4(Sup 2):27 [Abstract 017] (1999)

Thorlacius-Ussing, "Zinc in the anterior pituitary of rat: a histochemical and analytical work",*Neuroendocrinology*. 45(3):233–242 (1987)

Torres R, "Treatment of dorsocervical fat pads and truncal adiposity with Serostim (recombinant human growth hormone) in patients with AIDS maintained on HAART", Abstract 32164: 12$^{th}$ World AIDS Conference, Geneva [Abstract 32164] (1998)

Torres R et al, "The effect of Recombinant Human Growth Hormone on Protease-Inhibitor-Associated Fat Maldistribution Syndrome", Abstract 675: 6$^{th}$ Conference on Retroviruses and Opportunistic Infections [Abstract 675] (1999)

Viard et al, "Lipodystrophy syndromes in a cohort of HIV-1 infected patients receiving HAART with a protease inhibitor", *Antiviral Therapy* 4(Sup 2):32 [Abstract 026] (1999)

Viraben et al, "Indinavir-associated lipodystrophy", *AIDS* 12(6):F37–39 (1998)

Wanke et al, "Recombinant human growth hormone improves the fat redistribution syndrome (lipodystrophy) in patients with HIV", *AIDS* 13(15):2099–2103 (1999)

Windisch et al, "Recombinant human growth hormone for AIDS-associated wasting", *Ann Pharmacother* 32(4):437–45 (1998)

What is claimed is:

1. A method for treating HIV-associated dysmorphia/dysmetabolic syndrome (HADDS), comprising administering to a patient in need thereof an effective amount of a substance which is human growth hormone (hGH) or a functional derivative, fragment, variant, analog, or salt thereof which retains the biological activity of human growth hormone.

2. A method in accordance with claim 1, wherein said substance is an isolated human growth hormone.

3. The method according to claim 2, wherein said substance is recombinant human growth hormone.

4. The method according to claim 1, wherein said substance is administered subcutaneously.

5. The method according to claim 1, wherein said substance is administered intramuscularly.

6. The method according to claim 1, wherein said HADDS is abnormal visceral adipose tissue (VAT) accumulation and said patient is a HIV/AIDS patient presenting abnormal visceral adipose tissue accumulation.

7. The method according to claim 1, wherein said HADDS is dorsocervical adipose tissue accumulation ("buffalo hump") and said patient is a HIV/AIDS patient presenting dorsocervical adipose tissue accumulation ("buffalo hump").

8. The method according to claim 1, wherein said HADDS is another type of pathological adipose accumulation associated with HADDS syndrome selected from the group consisting of abnormal accumulation of adipose tissue in submandibular ("horse collar"), supraclavicular, pectoral and/or mammary areas, and/or has lipomas (benign encapsulated fatty tumors, either single or multiple), and said patient is a HIV/AIDS patient presenting with one or more of these abnormal features.

9. A method in accordance with claim 1, wherein said substance is methionyl hGH.

10. A method in accordance with claim 1, wherein said substance is 20-K-hGH, a naturally-occurring variant of hGH found in the pituitary and in the bloodstream.

11. A method in accordance with claim 1, wherein said substance is GH-V, a naturally-occurring variant of hGH found in the placenta.

12. A method in accordance with claim 1, wherein said substance is two-chain anabolic protein (2-CAP) formed by controlled proteolysis of hGH with trypsin.

13. A method in accordance with claim 1, wherein said substance is deamidated hGH.

14. A method in accordance with claim 1, wherein said substance is sulfoxidated hGH.

15. A method in accordance with claim 1, wherein said substance is hGH acetylated at the N-terminus.

16. A method for treating the pathological accumulation of adipose tissue in specific regional depots, comprising administering to a patient in need thereof an effective amount of a substance which is human growth hormone or a functional derivative, fragment, variant, analog, or salt thereof which retains the biological activity of human growth hormone.

17. A method in accordance with claim 16, wherein said substance is an isolated human growth hormone.

18. The method according to claim 17, wherein said substance is recombinant human growth hormone.

19. The method according to claim 16, wherein said substance is administered subcutaneously.

20. The method according to claim 16, wherein said substance is administered intramuscularly.

21. A method in accordance with claim 16, wherein said substance is methionyl hGH.

22. A method in accordance with claim 16, wherein said substance is 20-K-hGH, a naturally-occurring variant of hGH found in the pituitary and in the bloodstream.

23. A method in accordance with claim 16, wherein said substance is GH-V, a naturally-occurring variant of hGH found in the placenta.

24. A method in accordance with claim 16, wherein said substance is two-chain anabolic protein (2-CAP) formed by controlled proteolysis of hGH with trypsin.

25. A method in accordance with claim 16, wherein said substance is deamidated hGH.

26. A method in accordance with claim 16, wherein said substance is sulfoxidated hGH.

27. A method in accordance with claim 16, wherein said substance is hGH acetylated at the N-terminus.

* * * * *